United States Patent [19]

Shubkin et al.

[11] Patent Number: 4,725,681
[45] Date of Patent: Feb. 16, 1988

[54] PRODUCTION OF TRIETHYLENEDIAMINE

[75] Inventors: Ronald L. Shubkin; Duane C. Hargis, both of Baton Rouge, La.

[73] Assignee: Ethyl Corporation, Richmond, Va.

[21] Appl. No.: 767,137

[22] Filed: Aug. 19, 1985

[51] Int. Cl.$^4$ .................. C07D 487/18; C07D 295/08; C07D 295/12
[52] U.S. Cl. .................... 544/352; 544/401; 544/170; 544/402
[58] Field of Search ............................ 544/352, 401

[56] References Cited

U.S. PATENT DOCUMENTS

| | | | |
|---|---|---|---|
| 2,937,176 | 5/1960 | Herrick | 544/352 |
| 2,977,364 | 3/1961 | Mascioli | 544/352 |
| 3,056,788 | 10/1962 | Brader | 544/352 |
| 3,080,371 | 3/1963 | Spielberger et al. | 544/352 |
| 3,148,190 | 9/1964 | Swanson | 544/352 |
| 3,157,657 | 11/1964 | Brader, Jr. | 544/352 |
| 3,166,558 | 1/1965 | Mascioli | 544/352 |
| 3,172,891 | 3/1965 | Brader, Jr. et al. | 544/352 |
| 3,231,573 | 1/1966 | Brader, Jr. et al. | 544/352 |
| 3,242,183 | 3/1966 | Matell et al. | 544/352 |
| 3,285,917 | 11/1966 | Brader | 544/352 |
| 3,285,920 | 11/1966 | Muhlbauer | 544/352 |
| 3,297,701 | 1/1967 | Brader et al. | 544/352 |
| 3,342,820 | 9/1967 | Brader | 544/401 |
| 3,369,019 | 2/1968 | Hamilton et al. | 544/352 |
| 3,772,293 | 11/1973 | Oakes et al. | 544/352 |
| 4,017,494 | 4/1977 | Bosche et al. | 544/352 |
| 4,289,881 | 9/1981 | Imre et al. | 544/352 |
| 4,338,443 | 7/1982 | Brennen | 544/401 |
| 4,514,567 | 4/1985 | Wells | 544/352 |
| 4,521,600 | 6/1985 | Wells | 544/352 |

FOREIGN PATENT DOCUMENTS

| | | |
|---|---|---|
| 111928 | 6/1984 | European Pat. Off. ............ 544/352 |
| 1219491 | 7/1966 | Fed. Rep. of Germany . |
| 942868 | 7/1960 | United Kingdom . |

OTHER PUBLICATIONS

Ishiguru, J. Pharmaceutical Soc. Japan, 73, 1110–1114 (1953).
Ishiguru, J. Pharmaceutical Soc. Japan, 74, 1162–1165 (1954).
Ishiguru, J. Pharmaceutical Soc. Japan, 75, 674–677 (1955).
Ishiguru, J. Pharmaceutical Soc. Japan, 75, 1318–1321 (1955).
Ishiguru, J. Pharmaceutical Soc. Japan, 75, 1367–1369 (1955).
Ishiguru, J. Pharmaceutical Soc. Japan, 75, 1370–1373 (1955).
Chemical Abstracts, 38: 2627$^8$ (1944), [Abstract of Hromatka et al, Berichte 76B, 712–717 (1943)].
Hill et al, Industrial and Engineering Chemistry, 43, 1579–1583 (1951).
Chemical Abstracts, 1956, 10106j, [Abstract of Ishiguro et al., J. Pharm. Soc. Japan, 75, 1370–73 (1955)].

*Primary Examiner*—Mark L. Berch
*Attorney, Agent, or Firm*—Donald L. Johnson; John F. Sieberth

[57] ABSTRACT

An ethanolamine, preferably diethanolamine, is converted to triethylenediamine or 1,4-bis(2-hydroxyethyl)piperazine, or both by pyrolysis using a B-subgroup metal oxide such as titanium dioxide or zirconium dioxide, as catalyst. In addition it has also been discovered that 1,4-bis(2-hydroxyethyl)piperazine and N-(2-hydroxyethyl)piperazine can be converted in high yields and conversions into triethylenediamine by pyrolysis using the same type of catalyst. When using an ethanolamine as the feedstock and a Group IV-B metal oxide as the catalyst, the process usually results in the coproduction of triethylenediamine and 1,4-bis(2-hydroxyethyl)piperazine, and the latter can be recovered and used as a raw material for the production of additional triethylenediamine, as by recycle to the same reactor or as feedstock to an additional pyrolysis reactor.

19 Claims, No Drawings

PRODUCTION OF TRIETHYLENEDIAMINE

BACKGROUND

Triethylenediamine (1,4-diazabicyclo[2.2.2]octane), is useful as a catalyst in the production of polyurethanes. Various methods for its production have been reported heretofore.

THE INVENTION

Pursuant to this invention, a simple and economical pyrolytic process has been discovered whereby an ethanolamine can be converted to triethylenediamine or 1,4-bis(2-hydroxyethyl)piperazine, or both. In addition it has also been discovered that 1,4-bis(2-hydroxyethyl)-piperazine can be converted into triethylenediamine by a simple and economical pyrolytic process. And it has been discovered that N-(2-hydroxyethyl)piperazine may be converted by a pyrolytic reaction into triethylenediamine. In all of these processes the pyrolysis is conducted in the presence of a suitable catalyst, notably a B-subgroup metal oxide such as titanium dioxide, zirconium dioxide, and the like. When using an ethanolamine as the feedstock and a Group IV-B metal oxide as the catalyst, the process usually results in the coproduction of triethylenediamine and 1,4-bis(2-hydroxyethyl)-piperazine, and the latter can be recovered and used as a raw material for the production of additional triethylenediamine, as by recycle to the same reactor or as feedstock to an additional pyrolysis reactor.

Monoethanolamine, diethanolamine, triethanolamine, and any mixture of any two or all three of them can be used as feed to the process and as indicated above, any such ethanolamine feed may be utilized in conjunction with a feed of 1,4-bis(2-hydroxyethyl)piperazine. And in other embodiments of the invention, the feed to the process consists essentially of 1,4-bis(2-hydroxyethyl)-piperazine or N-(2-hydroxyethyl)piperazine, or mixtures of both of them. The ethanolamines may be represented by the formula, $(HOCH_2CH_2)_nNH_m$, where n is from 1 to 3 and m is from zero to 2, n plus m being 3. Of the ethanolamines, diethanolamine tends to give the highest yields of triethylenediamine. Thus preferred feedstocks for the process are (a) diethanolamine, (b) a mixture of ethanolamines composed predominantly of diethanolamine, and either (a) or (b) in admixture with 1,4-bis(2-hydroxyethyl)piperazine.

The pyrolysis is conducted at any suitable elevated temperature at which the desired product is formed. Usually the temperature will be above about 200° C. and preferably is at least about 300° C. The temperature of the reaction system should be kept below that at which the catalyst becomes inactive or excessive thermal decomposition of the desired product occurs. In most cases therefore the reaction will be conducted in the range of about 250° C. and about 350° C.

The process is capable of being carried out in either a batch or continuous mode of operation according to the available equipment and desires of the operator.

According to the invention, various B-subgroup metal oxide catalysts of suitable activity may be used. These include metal oxides of Groups I-B, II-B, III-B, IV-B, V-B, VI-B, VII-B, or mixtures thereof. As is well known, Group I-B is composed of copper, silver and gold whereas Group II-B is composed of zinc, cadmium and mercury. Scandium, yttrium and the lathanide and actinide series make up Group III-B. Group IV-B consists of titanium, zirconium and hafnium, Group V-B consists of vanadium, niobium and tantalum, Group VI-B consists of chromium, molybdenum and tungsten, and Group VII-B consists of manganese, technetium and rhenium. Various oxides of such metals that are viable catalysts for the reaction are within the ambit of this invention. Catalysts composed of mixtures of two or more different oxides of the same B-subgroup metal (e.g., $TiO_2$ and $Ti_2O_3$, etc.), composed of oxides of two or more different metals of the same B-subgroup (e.g., $TiO_2$ and $ZrO_2$; $TiO_2$, $ZrO_2$ and $HfO_2$, etc.), and composed of oxides of two or more metals of different B-subgroups (e.g., $TiO_2$ and $MoO_3$, $TiO_2$ and $WO_3$, $TiO_2$ and $ZnO$, etc.) may also be used. Various other oxides usable as additional components of the catalysts of the present invention such as one or more oxides of aluminum, antimony, barium, beryllium, bismuth, calcium, cobalt, gallium, germanium, iron, lead, magnesium, nickel, osmium, potassium, silicon, sodium, tin, and the like may be prepared by any of the known means and combined with the B-subgroup metal oxide catalysts according to the invention. Catalysts composed of one or more B-subgroup metal oxides in combination with one or more non-B-subgroup metal oxides should predominate (on a molar basis) in the B-subgroup metal oxide(s). In fact, such mixed oxide catalysts preferably contain at least 70 mole % of one or more B-subgroup metal oxides and no more than about 30 mole % of one or more non-B-subgroup metal oxides.

It is important when practicing this invention to use an active catalyst for the process. In this connection, the thermal history of the catalyst may be of importance to its activity. For example, a highly active catalyst for the process may lose all or a portion of its activity if heated to excessively high temperatures. Thus any given commercially available catalysts, especially a Group IV-B metal oxide catalyst may or may not be active in the process of this invention depending upon whether or not it was calcined and if so, whether the calcining temperature was high enough to destroy its catalytic activity for use in the process of this invention. Thus in selecting commercially available catalysts for use in the process, one should attempt to secure materials that have not been calcined at excessively high temperatures that render them unsuitable in the present process. In cases where the manufacturers decline to supply such thermal history information, one should secure and test in the present process a variety of samples of candidate catalysts and select one or more having suitable activity for the process.

Methods for the manufacture of the oxides of B-subgroup metals are known and reported in the literature. When utilizing such procedures care should be taken to avoid heating the catalyst to a temperature which destroys or substantially diminishes its catalytic activity in the synthesis process of this invention. The catalyst may be supported on or impregnated onto a suitable inert carrier although this is ordinarily unnecessary.

Although the process can be carried out in the liquid phase, it is preferable to conduct the process in the vapor phase using a fixed-bed or a moving or fluidized bed of the catalyst.

Co-feeding hydrogen, ammonia, or water with the amine reactant(s) tends to give small increases in yield of triethylenediamine.

The present invention will be still further understood by a review of the following illustrative examples, in which all percentages are expressed on a weight basis unless otherwise specified.

In the ensuing examples the reactions were carried out in a one-inch inside diameter stainless steel, tubular reactor heated with an external furnace. A 20 cc charge of titanium dioxide pellets (Harshaw Ti 0720 T ⅛) was supported in the reactor on glass beads. Temperature was measured by a thermocouple located in the catalyst bed. Liquid feed of the amine reactant (and water, when used) was introduced into the reactor (at 4 mL/hr unless otherwise specified), and liquid product from the reactor was collected in a trap cooled by an ice bath. At the conclusion of a run, the reactor was cooled and washed with methanol solvent. The methanol was stripped off and the residue was combined with the liquid product. The combined product was then analyzed by means of a gas chromatograph.

EXAMPLE 1

Feed: Diethanolamine, plus helium at 600 mL/hr
Reaction temperature: 250° C.
Diethanolamine conversion: 81%
Yields:
    Triethylenediamine (TEDA) - 5.4%
    1,4-Bis(2-hydroxyethyl)piperazine (BHEP) - 19.7%

EXAMPLE 2

Feed: Diethanolamine, plus hydrogen at 600 mL/hr
Reaction temperature: 250° C.
Diethanolamine conversion: 76%
Yields:
    TEDA - 7.9%
    BHEP - 21.8%

EXAMPLE 3

Feed: diethanolamine, plus ammonia at 600 mL/hr
Reaction temperature: 250° C.
Diethanolamine conversion: 79%
Yields:
    TEDA - 7.9%
    BHEP - 19.7%

EXAMPLE 4

Feed: Diethanolamine plus water (1:2 molar)
Reaction temperature: 250° C.
Diethanolamine conversion: 60%
Yields:
    TEDA - 6.2%
    BHEP - 23.2%

EXAMPLE 5

Feed: Diethanolamine (2 ML/hr)
Reaction temperature: 250° C.
Diethanolamine conversion: 88%
Yields:
    TEDA - 2.6%
    BHEP - 25.1%

EXAMPLE 6

Feed: Diethanolamine
Reaction temperature: 300° C.
Diethanolamine conversion: 87%
Yields:
    TEDA - 20.3%
    BHEP - 4.8%

EXAMPLE 7

Feed: Ethanolamine and diethanolamine (1:1 molar)
Reaction temperature: 250° C.
Ethanolamine conversion: 35%
Diethanolamine conversion: 79%
Yields (based on converted diethanolamine only):
    TEDA - 12.0%
    BHEP - 10.0%

EXAMPLE 8

Feed: Ethanolamine and diethanolamine (1:1 molar)
Reaction temperature: 300° C.
Ethanolamine conversion: 62%
Diethanolamine conversion: 91%
Yields (based on converted diethanolamine only):
    TEDA - 18.2%
    BHEP - 6.4%

EXAMPLE 9

Feed: 1,4-Bis(2-hydroxyethyl)peperazine (BHEP) plus water (40:60 wt ratio)
Reaction temperature: 275° C.
BHEP conversion: 96%
TEDA Yield: 50.9%

EXAMPLE 10

Feed: 1,4-Bis(2-hydroxyethyl)piperazine (BHEP) plus water (40:60 wt ratio)
Reaction temperature: 300° C.
BHEP conversion: 96%
TEDA Yield: 42.5%

EXAMPLE 11

Feed: N-(2-hydroxyethyl)piperazine (HEP) plus water 57:43 wt ratio)
Reaction temperature: 275° C.
HEP conversion: 84%
TEDA Yield: 41.1%

EXAMPLE 12

Feed: Triethanolamine plus water (75:25 ratio)
Reaction temperature: 250° C.
Triethanolamine conversion: 85%
Yields:
    TEDA - 1.7%
    4-Hydroxyethylmorpholine - 11.9%

EXAMPLE 13

Feed: Triethanolamine plus water (75:25 wt ratio)
Reaction temperature: 300° C.
Triethanolamine conversion: 100%
Yields:
    TEDA - 7.7%
    4-Hydroxyethylmorpholine - 1.7%

EXAMPLE 14

Feed: Ethanolamine
Reaction temperature: 300° C.
Ethanolamine conversion: 79%
Yields:
    TEDA - 0.7%
    Piperazine - 8.1%
    N-(2-Aminoethyl)piperazine - 7.6%

The high conversions and yields in Examples 9–11 are noteworthy.

While this invention has been described with reference to use of ethanolamines and 2-hydroxyethyl substituted piperazines in the process it is contemplated that similar products may be produced by use of their analogues and higher homologues such as propanolamine, dipropanolamine, tripropanolamine, 1,4-bis(3-hydroxypropyl)piperazine, N-ethyldiethanolamine, and the like.

Inasmuch as this invention is susceptible to considerable variation in its practice without departing from its true spirit and scope, it is not intended that it be limited by the illustrative disclosure herein presented. Rather, the scope of this invention is to be defined with reference to the ensuing claims and the equivalents thereof to which the invention is entitled by law.

What is claimed is:

1. A process which comprises contacting an ethanolamine composed predominantly of diethanolamine and a B-subgroup metal oxide catalyst containing at least 70 mole percent of titanium dioxide at an elevated temperature at which triethylenediamine or 1,4-bis(2-hydroxyethyl)piperazine, or both, are formed, said ethanolamine having the formula $(HOCH_2CH_2)_nNH_m$, where n is from 1 to 3 and m is from zero to 2, n plus m being 3.

2. A process of claim 1 in which the ethanolamine is diethanolamine.

3. A process of claim 1 in which the B-subgroup metal oxide catalyst consists essentially of titanium dioxide.

4. A process of claim 1 in which the temperature is at least about 300° C.

5. A process of claim 1 in which the ethanolamine is contacted in the vapor phase with the catalyst.

6. A process which comprises contacting an ethanolamine composed predominantly of diethanolamine in the vapor phase and a Group IV-B metal oxide catalyst containing at least 70 mole percent of titanium dioxide at an elevated temperature of at least about 300° C. at which triethylenediamine or 1,4-bis(2-hydroxyethyl)-piperazine, or both, are formed, said ethanolamine having the formula $(HOCH_2CH_2)_nNH_m$, where n is from 1 to 3 and m is from zero to 2, n plus m being 3.

7. A process of claim 6 in which the ethanolamine is diethanolamine.

8. A process of claim 6 in which the B-subgroup metal oxide catalyst consists essentially of titanium dioxide.

9. A process for the production of triethylenediamine which comprises contacting (i) a feed mixture comprising 1,4-bis(2-hydroxyethyl)piperazine and diethanolamine, and (ii) a B-subgroup metal oxide catalyst which consists essentially of titanium dioxide at an elevated temperature at which triethylenediamine is formed.

10. A process for the production of triethylenediamine which comprises:
   (a) contacting an ethanolamine composed predominantly of diethanolamine and a B-subgroup metal oxide catalyst which consists essentially of titanium dioxide or zirconium dioxide, or both, at an elevated temperature at which triethylenediamine and 1,4-bis(2-hydroxyethyl)piperazine are formed,
   (b) recovering and separating triethylenediamine and 1,4-bis(2-hydroxyethyl)piperazine so formed, and
   (c) contacting the 1,4-bis(2-hydroxyethyl)piperazine and a B-subgroup metal oxide catalyst which consists essentially of titanium dioxide or zirconium dioxide, or both, at an elevated temperature at which additional triethylenediamine is formed, said ethanolamine of step (a) having the formula $(HOCH_2CH_2)_nNH_m$, where n is from 1 to 3 and m is from zero to 2, n plus m being 3.

11. A process of claim 10 in which the ethanolamine of step (a) is diethanolamine.

12. A process of claim 10 in which the B-subgroup metal oxide catalyst consists essentially of titanium dioxide.

13. A process of claim 10 in which the ethanolamine of step (a) is diethanolamine and in which the B-subgroup metal oxide catalysts consists essentially of titanium dioxide.

14. A process of claim 10 in which the ethanolamine in step (a) and the 1,4-bis(2-hydroxyethyl)piperazine in step (c) are in the vapor phase.

15. A process for the production of triethylenediamine which comprises:
   (a) contacting (i) an ethanolamine composed predominantly of diethanolamine and (ii) 1,4-bis(2-hydroxyethyl)piperazine, and a B-subgroup metal oxide catalyst which consists essentially of titanium dioxide or zirconium dioxide, or both, at an elevated temperature at which triethylenediamine and 1,4-bis(2-hydroxyethyl)piperazine are formed,
   (b) recovering and separating triethylenediamine and 1,4-bis(2hydroxyethyl)piperazine so formed, and
   (c) recycling the 1,4-bis(2-hydroxyethyl)piperazine to step (a), said ethanolamine of step (a) having the formula $(HOCH_2CH_2)_nNH_m$, where n is from 1 to 3 and m is from zero to 2, n plus m being 3.

16. A process of claim 15 in which the ethanolamine of step (a) is diethanolamine.

17. A process of claim 15 in which the B-subgroup metal oxide catalyst consists essentially of titanium dioxide.

18. A process of claim 15 in which the ethanolamine of step (a) is diethanolamine and in which the B-subgroup metal oxide catalyst consists essentially of titanium dioxide.

19. A process of claim 15 in which the ethanolamine and the 1,4-bis(2-hydroxyethyl)piperazine in step (a) are in the vapor phase.

* * * * *